(12) United States Patent
Hurst et al.

(10) Patent No.: US 11,511,009 B2
(45) Date of Patent: Nov. 29, 2022

(54) FILTERED PRODUCT BAG WITH COMPACT FORM FACTOR

(71) Applicants: BAXTER INTERNATIONAL INC., Deerfield, IL (US); BAXTER HEALTHCARE SA, Glattpark (CH)

(72) Inventors: William Spencer Hurst, Burlington, WI (US); Steven Clarence Jepson, Vernon Hills, IL (US); Grant Anthony Bomgaars, Kildeer, IL (US); Yuanpang Samuel Ding, Long Grove, IL (US); Thomas Edward Dudar, Palatine, IL (US); Ying-Cheng Lo, Long Grove, IL (US); Bernd Krause, Rangendingen (DE); Mark Edward Pasmore, Grayslake, IL (US); Michael Joseph Sadowski, Ringwood, IL (US); Anastasios Hristakos, Evanston, IL (US); Joseph Vincent Ranalletta, Greenville, SC (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 499 days.

(21) Appl. No.: 16/631,067

(22) PCT Filed: Jul. 12, 2018

(86) PCT No.: PCT/US2018/041809
§ 371 (c)(1),
(2) Date: Jan. 14, 2020

(87) PCT Pub. No.: WO2019/018202
PCT Pub. Date: Jan. 24, 2019

(65) Prior Publication Data
US 2020/0147251 A1    May 14, 2020

Related U.S. Application Data

(60) Provisional application No. 62/533,427, filed on Jul. 17, 2017.

(51) Int. Cl.
*A61L 2/26*    (2006.01)
*B65B 3/00*    (2006.01)
(Continued)

(52) U.S. Cl.
CPC ............ *A61L 2/26* (2013.01); *B65B 3/003* (2013.01); *A61J 1/10* (2013.01); *A61J 1/1456* (2015.05);
(Continued)

(58) Field of Classification Search
CPC ...... A61L 2/26; A61L 2/022; A61L 2202/121; A61L 2202/181; A61L 2202/21;
(Continued)

(56) References Cited

U.S. PATENT DOCUMENTS

| 4,235,233 A | * | 11/1980 | Mouwen | A61J 1/10 |
| | | | | 604/406 |
| 2014/0012185 A1 | * | 1/2014 | Ishizuka | A61M 1/32 |
| | | | | 604/416 |

FOREIGN PATENT DOCUMENTS

| EP | 2684551 A1 | 1/2014 |
| WO | WO-02085111 A1 | 10/2002 |

OTHER PUBLICATIONS

Australian Patent Application No. 2018304077, Examination Report, dated May 3, 2022.
(Continued)

*Primary Examiner* — Regina M Yoo
(74) *Attorney, Agent, or Firm* — Marshall, Gerstein & Borun LLP

(57) ABSTRACT

A product bag includes a bladder and an elongated filtration device. The bladder includes opposing first and second film
(Continued)

layers defining a product chamber. The first and second film layers are sealed together along a perimeter seal extending along at least a portion of a perimeter of the bladder. The elongated filtration device includes a housing, a filtration membrane disposed in the housing, an inlet adapted for receiving a fluid to be filtered, and an outlet in fluid communication with the product chamber. A majority of the elongated filtration device is embedded between the first and second film layers of the perimeter seal of the bladder to provide for a compact form factor.

6 Claims, 11 Drawing Sheets

(51) Int. Cl.
  *A61J 1/14*    (2006.01)
  *A61J 1/10*    (2006.01)
  *A61L 2/02*    (2006.01)

(52) U.S. Cl.
  CPC ......... *A61L 2/022* (2013.01); *A61L 2202/121* (2013.01); *A61L 2202/181* (2013.01); *A61L 2202/21* (2013.01); *A61M 2207/00* (2013.01)

(58) Field of Classification Search
  CPC ..... A61L 2202/123; A61J 1/10; A61J 1/1456; B65B 3/003; B65B 3/006
  See application file for complete search history.

(56) References Cited

OTHER PUBLICATIONS

Written Opinion for International Application No. PCT/US2018/041809, dated Oct. 29, 2018.
International Search Report for International Application No. PCT/US2018/041809, dated Oct. 29, 2018.

* cited by examiner

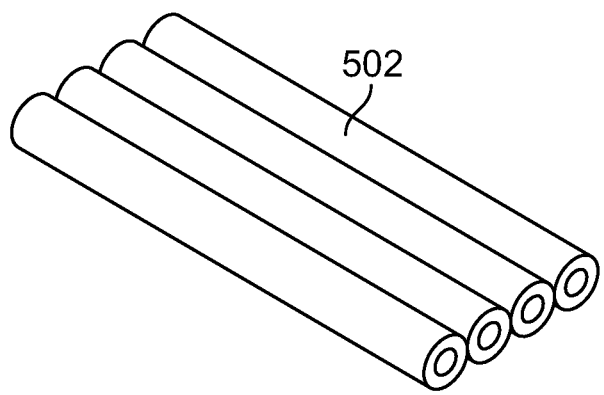
FIG. 13
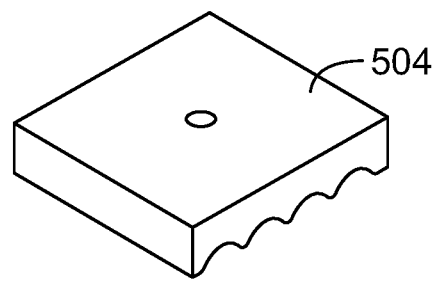
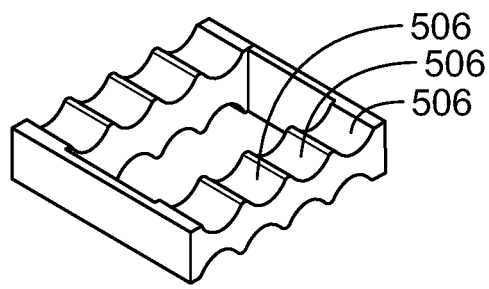
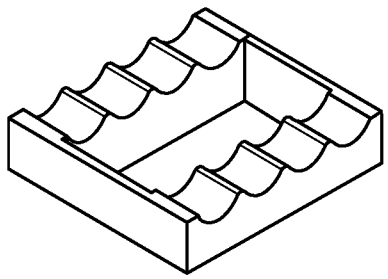
FIG. 14

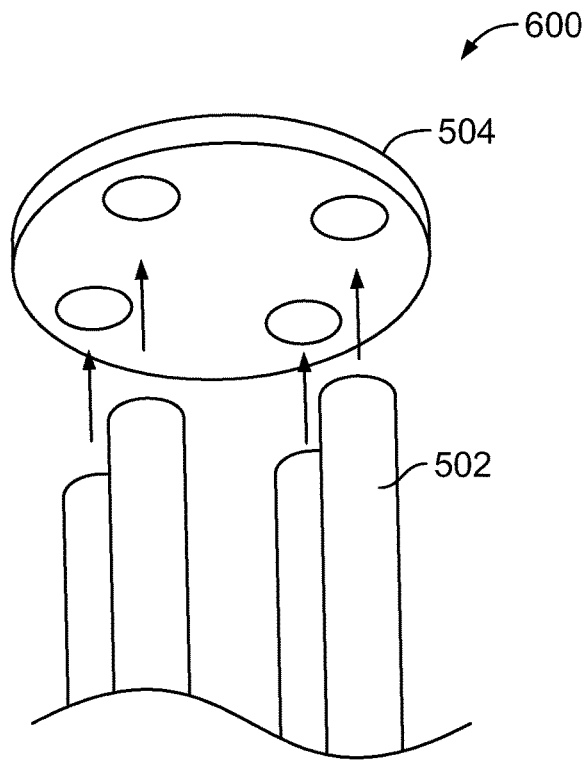
FIG. 15
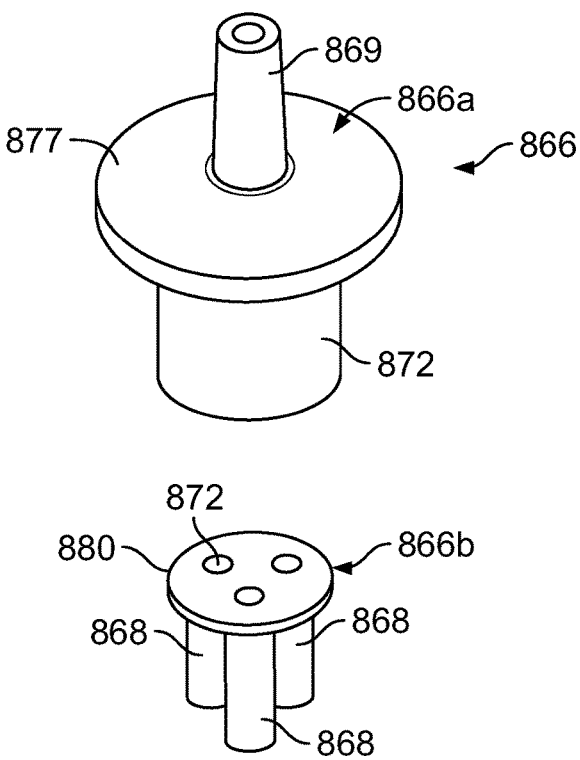
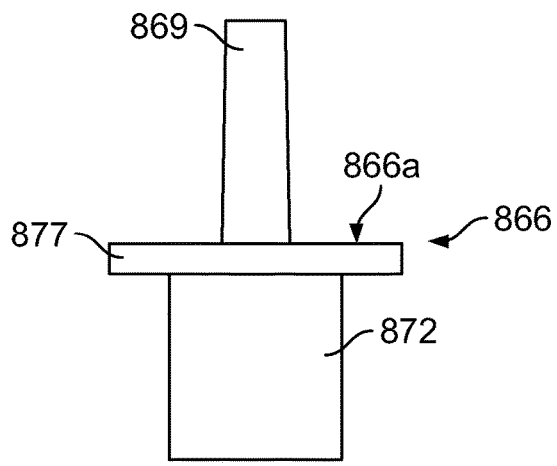
FIG. 16
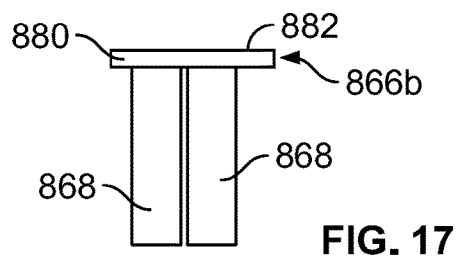
FIG. 17

FILTERED PRODUCT BAG WITH COMPACT FORM FACTOR

CROSS-REFERENCE TO AND RELATED APPLICATIONS

This is the United States national phase of PCT/US18/41809, filed Jul. 12, 2018, which claims the priority benefit of U.S. Provisional Application Ser. No. 62/533,427, filed Jul. 17, 2017, the entire contents of each of which are incorporated herein by reference.

Additionally, the following related and co-owned U.S. applications are hereby expressly incorporated herein by reference in their entirety: U.S. Provisional Application Ser. No. 62/533,362, having (entitled STERILE PRODUCT BAG WITH FILTERED PORT); U.S. Provisional Application Ser. No. 62/533,380, having (entitled DUAL CONTAINER SYSTEM FOR PRODUCT RECONSTITUTION); U.S. Provisional Application Ser. No. 62/533,408, having (entitled MEDICAL PRODUCT INCLUDING PRE-FILLED PRODUCT BAG WITH FILTERED FLUID PORT); and U.S. Provisional Application Ser. No. 62/533,440, having (entitled MEDICAL SYRINGE SYSTEM WITH FILTERED FILLING PORT), each filed on Jul. 17, 2017.

FIELD OF THE DISCLOSURE

This disclosure relates to a product bag and, more particularly, a product bag having an integral filter that allows microbial and particulate matter filtration during filling in non-traditional settings.

BACKGROUND

Conventional methods for manufacturing bags of sterile solution, for example, include filling bags in a clean environment with a solution, sealing the filled bag of solution, and then sterilizing the fluid and bags in a sterilizing autoclave. This can be referred to as terminal sterilization. Another conventional method is to provide a sterile solution and fill and seal sterile bags in an extremely high-quality environment designed and controlled to prevent contamination of the solution during the filling process and to seal the filled bag. This can be referred to as an aseptic filling process.

Terminal sterilization generally requires autoclaves to produce the sterilizing heat and steam needed. These autoclaves generally are not economical unless they can produce large batches of terminally sterilized bags. Thus the capital expenditure needed and space requirements lead to centralized manufacturing facilities that produce the filled bags, sterilize the bags and then ship them some distance to their destination for use. Also, the application of terminal sterilization processes may degrade the solution formulation thereby leading to incompatible or unstable formulations.

The aseptic manufacturing process must occur in a sterile working environments, and require expensive equipment, stringent procedures and extensive monitoring to ensure that solution product bags meet certain environmental and manufacturing regulatory standards. Sterilizing a working environment, by itself, can be costly and time consuming. Technicians involved in the filling process must also follow rigorous operational protocols to ensure the environment is not contaminated so as to produce safe and sterile products. Even with these safeguards, unless it can be verified that the solution entering the bag is sterile, there is a risk that contaminants may have inadvertently been introduced into the solution during filling/sealing, and once introduced, unless the solution later passes through a viable sterilizing filter, the contaminants will remain in the solution. Again due to these requirements, sterile solution product bags are often produced in centralized locations and shipped some distance to their destination for use.

Considering the costs associated with manufacturing sterile solution product bags, most health centers and clinics outsource the production of bags of sterile solutions to companies having the facilities to produce large quantities of bags of sterile solutions. As noted above, due to the capital and other requirements to produce bags of sterile solutions, the production is centralized in a small number of large production facilities and the resulting production is transported sometimes long distances to the user. To maintain the sterility of the shipment of bags travelling long distances, the sterile product bags must be carefully packaged and shipped to ensure safe delivery. These packaging and transport distances can increase the cost of the bags for the user.

SUMMARY

A first aspect of the present disclosure provides a product bag having a bladder and an elongated filtration device. The bladder includes opposing first and second film layers defining a product chamber. The first and second film layers are sealed together along a perimeter seal extending along at least a portion of a perimeter of the bladder. The elongated filtration device includes a housing, a filtration membrane disposed in the housing, an inlet adapted for receiving a fluid to be filtered, and an outlet in fluid communication with the product chamber. A majority of the elongated filtration device is embedded between the first and second film layers of the perimeter seal of the bladder to provide for a compact form factor.

In a second aspect, the product bag further includes a retention section of the perimeter seal, and an elongated retention channel disposed in the retention section. The retention section has a length dimension greater than a width dimension. The elongated retention channel is disposed between the first and second film layers in the retention section and extends along the length dimension of the retention section. The retention channel contains the majority of the elongated filtration device.

In a third aspect, at least a portion of the housing of the filtration device is hermetically sealed to at least a portion of the retention channel at a port seal.

In a fourth aspect, the product bag further includes a bridging channel extending between the retention channel and the product chamber to provide fluid communication between the filtration device and the product chamber.

In a fifth aspect, the first and second film layers are constructed of a heat sealable polymer material.

In a sixth aspect, the bladder is generally rectangular in shape having opposite first and second short sides and opposite first and second long sides, and wherein the filtration device is embedded in the perimeter seal along the first long side.

In a seventh aspect, the product bag further includes an outlet port in fluid communication with the product chamber for administering product from the product bag to a patient.

In a eighth aspect, the filter membrane has a nominal pore size in a range of approximately 0.1 µm to approximately 0.5 µm.

In a ninth aspect, the filter membrane is shaped as a hollow fiber with a wall and pores residing in the wall of the fiber.

In a tenth aspect, the product chamber comprises first and second chamber portions isolated from each other by a chamber seal.

In an eleventh aspect, the filter membrane comprises a plurality of filter membranes.

In a twelfth aspect, the filter membrane includes an outlet end that is sealed and an inlet end that is an open inlet.

In a thirteenth aspect, the filter membrane has a wall thickness in the range of approximately 150 µm to approximately 500 µm.

In a fourteenth aspect, the filter membrane has a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

In a fifteenth aspect, the filter membrane is made of at least one of the following materials: a polyolefin, polyvinylidene fluoride, polymethylmethacrylate, polyacrylonitrile, polysulfone, polyethersulfone, and a polymer containing cationic charges.

In a sixteenth aspect, the housing of the filtration device is made of at least one of the following materials: PVC, PET, a poly(meth)acrylate, a polycarbonate, a polyolefin, a cycloolefin copolymer, polystyrene, or a silicone polymer.

In a seventeenth aspect, the filter membrane includes at least one U-shaped hollow fiber filter membrane secured in a U-shaped configuration by a filter membrane housing contained within a filter body.

In an eighteenth aspect, the filter includes a plurality of U-shaped hollow fiber filter membranes.

In a nineteenth aspect, the filter membrane comprises a plurality of parallel hollow fiber membrane filters secured in a side-by-side configuration.

In a twentieth aspect, the filter membrane comprises a plurality of parallel hollow fiber membrane filters arranged in a circular pattern.

In a twenty-first aspect, the product chamber is a sterile product chamber.

In a twenty-second aspect, the product bag further includes a medicinal or nutritional concentrate disposed in the product chamber.

A twenty-third aspect of the present disclosure includes a method of sterilizing and introducing fluid into a product bag. The method includes providing a bladder comprising opposing first and second film layers defining a sterile product chamber, the first and second film layers sealed together along a perimeter seal extending along at least a portion of a perimeter of the bladder, the perimeter seal including at least one break defining a bridging channel in fluid communication with the sterile product chamber. The method further includes providing a filtration device having an inlet end adapted for receiving a fluid to be sterilized, and an outlet end in fluid communication with the sterile product chamber via the bridging channel, the filtration device having a filter membrane with a nominal pore size in a range of approximately 0.1 µm to approximately 0.5 µm. The method further includes introducing a pharmaceutical fluid into the sterile product chamber through the filtration device and bridging channel such that a sterile pharmaceutical fluid resides within the sterile product chamber. The method further includes sealing the opposing first and second layer films together across the bridging channel to create a bridge seal to maintain the sterilized pharmaceutical fluid in the sterile product chamber.

In a twenty-fourth aspect, the method further includes cutting the filtration device off of the product bag.

In a twenty-fifth aspect, cutting the filtration device off of the product bag comprises cutting across the bridging seal.

In a twenty-sixth aspect, the method further includes performing a filter integrity test on the filter membrane after cutting the filtration device off of the product bag.

In a twenty-seventh aspect, performing the filter integrity test comprises performing one of a pressure degradation test, a bubble point test, a water intrusion test, or a water flow test.

In a twenty-eighth aspect, sealing the opposing first and second film layers together includes heat sealing the first and second film layers together to provide a hermetic seal.

In a twenty-ninth aspect, introducing the pharmaceutical fluid into the sterile product chamber through the filtration device comprises introducing the pharmaceutical fluid through a plurality of filter membranes.

In a thirtieth aspect, introducing the pharmaceutical fluid into the sterile product chamber through the filtration device comprises introducing the pharmaceutical fluid through an open outlet end and a sealed outlet end of a hollow fiber of the filter membrane.

In a thirty-first aspect, introducing the pharmaceutical fluid into the sterile product chamber through the filtration device comprises introducing the pharmaceutical fluid through a filter membrane having a wall thickness in the range of approximately 150 µm to approximately 500 µm.

In a thirty-second aspect, introducing the pharmaceutical fluid into the sterile product chamber through the filtration device comprises introducing the pharmaceutical fluid through a filter membrane having a longitudinal dimension in the range of approximately 3 cm to approximately 420 cm, an inner diameter in the range of approximately 2 mm to approximately 4 mm, and an outer diameter in the range of approximately 2.3 mm to approximately 5 mm.

In a thirty-third aspect, introducing the pharmaceutical fluid into the sterile product chamber through the filtration device comprises introducing the pharmaceutical fluid through a filter membrane made of at least one of the following materials: a polyolefin, polyvinylidene fluoride, polymethylmethacrylate, polyacrylonitrile, polysulfone, polyethersulfone, and a polymer containing cationic charges.

In a thirty-fourth aspect, introducing the pharmaceutical fluid into the sterile product chamber through the filtration device comprises introducing the pharmaceutical fluid through a filter having at least one U-shaped hollow fiber filter membrane secured in a U-shaped configuration by a filter membrane housing contained within a filter body.

In a thirty-fifth aspect, introducing the pharmaceutical fluid through a filter having at least one U-shaped hollow fiber filter membrane comprises introducing diluent through a plurality of U-shaped hollow fiber filter membranes.

In a thirty-sixth aspect, introducing the pharmaceutical fluid into the sterile product chamber through the filtration device comprises introducing the pharmaceutical fluid through a plurality of parallel hollow fiber membrane filters secured in a side-by-side configuration.

In a thirty-seventh aspect, introducing the pharmaceutical fluid into the sterile product chamber through the filtration device comprises introducing the pharmaceutical fluid through a plurality of parallel hollow fiber membrane filters arranged in a circular pattern.

In a thirty-eighth aspect, introducing the pharmaceutical fluid into the sterile product chamber through the filtration device comprises introducing the pharmaceutical fluid through a filter membrane having a nominal pore size in a range of approximately 0.1 μm to approximately 0.22 μm.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 13 is a front view of a plurality of hollow fiber membranes secured side by side;

FIG. 14 is an isometric view of the securement device used for the plurality of hollow fiber membranes depicted in FIG. 13;

FIG. 15 is an isometric view of a fiber bundle for a product bag having a plurality of hollow fiber membranes secured in a circular holder;

FIG. 16 is an exploded perspective view of an alternative connector for use with a three-filter filter bundle;

FIG. 17 is a side exploded view of the connector of FIG. 16;

DETAILED DESCRIPTION

Figure 1:
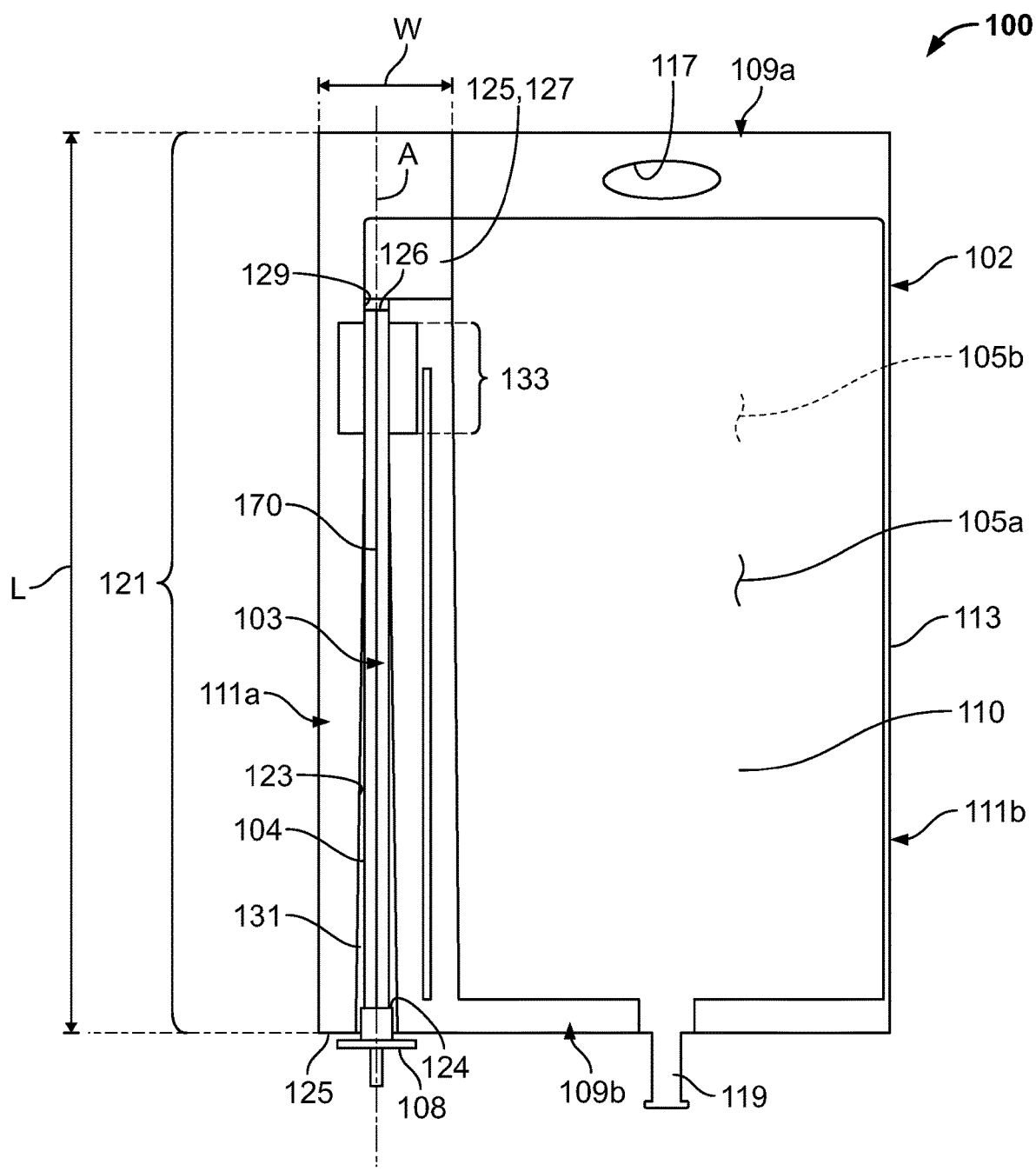
FIG. 1 is a front view of a first embodiment of a filtered product bag constructed in accordance with the principles of the present disclosure.

The present disclosure is directed to a novel device and method related to sterilizing and introducing pharmaceutical fluids (e.g., solutions, diluents, drug products, etc.) into a sterile product bag in cost-effective manner. The device includes a product bag constructed of two or more films sealed at a perimeter seal and defining a chamber such as in typical medical grade solution bags. Additionally, however, the product bag includes a sterilizing filtration device such that non-sterile pharmaceutical fluids can be introduced into the product bag in non-traditional environments such as hospitals and/or pharmacies. Uniquely, the filtration device is embedded into the perimeter seal of the product bag in a manner that facilitates filling, and subsequently sealing of the bag, removal and testing of the filter. Embedding the filtration device into the perimeter seal provides a compact configuration which adapts well to conventional manufacturing, sterilizing, shipping, and storage practices.

FIGS. 1 and 2A-2C illustrate a first embodiment of a product bag 100 constructed in accordance with the principles of the present disclosure. The product bag 100 includes a bladder 102 and a filtration device 103 embedded into the bladder 102 to provide a compact form factor susceptible to conventional sterilization, shipping, handling, storage, and other procedures. In more detail, one embodiment of the bladder 102 includes at least first and second opposing film layers 105a, 105b bonded together along a perimeter seal 107 and forming a product chamber 110. In other versions, the first and/or second film layers 105a, 105b can include multi-layer film products for protecting the contents of the product bag 100 against degradation due to light exposure or other environmental concerns. In the depicted version, the bladder 102 is generally rectangular in shaped having opposite top and bottom short sides 109a, 109b and opposite left and right long sides 111a, 111b. Additionally, as depicted, this embodiment, the perimeter seal 107 extends only along the top side 109a, left side 111a, and bottom side 109b. This is because the depicted version of the bladder 102 is constructed from a single piece of film folded in half at a seam 113 to form the right side 111b. Thus, in this version, the first and second film layers 105a, 105b are portions of a common sheet of film. In other versions, the perimeter seal 107 can also extend along the seam 113 at the right side 111b of the bladder 102. In still other embodiments, the first and second film layers 105a, 105b can be separate sheets such that the perimeter seal 107 also extends along the right side 111b in order to bond the sheets together to form the chamber 110. As further illustrated in FIG. 1, the product bag 100 can include an opening 117 disposed through the perimeter seal 107 at the top side 109a and an outlet port 119 extending through the perimeter seal 107 at the bottom side 109b. The opening 117 can be for hanging the product bag 100, while the outlet port 119 extends through the perimeter seal 107 in fluid communication with the chamber 110 for delivering contents of the product bag to an administration set during patient administration, for example.

With continued reference to FIG. 1 and as mentioned, the product bag 100 includes the filtration device 103 embedded in the bladder 102 for a compact product configuration. More particularly, as shown, the filtration device 103 is embedded into the perimeter seal 107 along the left side 111a of the product bag 100. That is, the perimeter seal 107 at the left side 111a of the product bag 100 includes a retention section 121 that extends from the bottom side 109b to the top side 109a of the bag 100 and has a length dimension L that is greater than a width dimension W. So configured, the retention section 121 is an elongated section of the perimeter seal 107 having a longitudinal axis A extending along the left side 111a of the product bag 100 parallel to the chamber 110. The retention section 121 moreover retains the filtration device 103 within a retention channel 123 defined between the first and second film layers 105a, 105b that are bonded together to form the perimeter seal 107. Similar to the retention section 121, the retention channel 123 is elongated and extends from the bottom side 109b of the product bag 100 almost entirely to the top side 109a. In the disclosed embodiment, the retention channel 123 extends parallel to and/or co-axial with the longitudinal axis A of the retention section 121. At the bottom side 109b, the retention channel 123 includes an inlet 125 and the opposite end of the retention channel 123 terminates at an outlet 129. The outlet 129 is located at a break 125 in the perimeter seal 107, which can be referred to as a bridging channel 127 that provides fluid communication between the retention channel 123 and the product chamber 110. As can be seen in FIG. 1, in one embodiment of the product bag 100 of the present disclosure, the retention channel 123 is tapered from the inlet 125 to the outlet 129. That is, a substantial portion of the cross-sectional diameter of the retention channel 123 converges from the inlet 125 to the outlet 129. This converging or tapered geometry can assist with installing the filtration device 103 in the retention channel 123 as will be described.

The filtration device 103 of the product bag 100 of the present disclosure can take many different forms suitable to sterilize fluids as they pass through the filtration device 103 and into the product chamber 110. The embodiment of the filtration device 103 depicted in FIG. 1 is elongated and extends parallel to and/or co-axially with the longitudinal axis A of the retention section 121 of the perimeter seal 107 such that a majority, if not all, of the filtration device 103 is embedded within the perimeter seal 107.

The filtration device 103 can include a housing 104, a filter membrane 170 disposed in-line with the housing 104, and a sterile closure cap and connector assembly 108. The housing 104 is a hollow narrow tube of uniform diameter fixed in the retention channel 123 of the retention section 121 of the perimeter seal 107. The housing 104 includes an inlet 124 disposed in proximity to the inlet 125 of the retention channel 123, and an outlet 126 disposed in proximity to the outlet 129 of the retention channel 123. In the depicted version, the sterile closure cap and connector assembly 108 can be disposed outside of the retention channel 123, as shown, or inside of the retention channel 123.

As mentioned above, the disclosed embodiment of the retention chamber 123 optionally includes a tapered or convergent geometry. Thus, the inlet 125 of the retention chamber 123 has a diameter that is greater than a diameter of the housing 104 of the filtration device 103, and the outlet 129 of the retention chamber 123 has a diameter that is substantially similar to the diameter of the housing 104 of the filtration device 103. Thus, an elongated annular gap 131 is present between a portion of the filtration device 103 and an interior wall of the retention chamber 123. An inner diameter of the gap 131 is constant, but an outer diameter of the gap 131 converges from the inlet 125 of the retention chamber 123 toward the outlet 129, where the diameters of the retention chamber 123 and filtration device 103 become similar. In the disclosed embodiment, there is a band 133 where the housing 104 of the filtration device 103 and the retention chamber 123 have a common diameter and where the two components are bonded together with a hermetic seal, which can be referred to as a port seal. The tapered or converging retention chamber 123 can assist with inserting the filtration device 103 into the retention chamber 123. It should be appreciated that in other embodiments, the geometrical relationship between the filtration device 103 and the retention channel 123 can vary, and a hermetic seal can be provided in order to ensure and maintain a sterile environment within the product chamber 110 before, during, and after use of the product bag 100. In other embodiments, a mechanical "tack seal" between container the film and the connector assembly 108 may be formed at the inlet 125 to provide mechanical stability of the container during handling, but a hermetic seal at inlet 125 may not be included or be necessary. In some embodiments, the entirety of the retention chamber 123 and housing 104 of the filtration device 103 can share a common diameter and the hermetic seal can extend along the entire length of the filtration device 103. In such an embodiment, the perimeter seal 107 may be formed for example with the filtration device 103 already in position between the first and second film layers 105a, 105b, as opposed to requiring the filtration device 103 to be inserted into the retention chamber 123 after the seal 107 has been formed.

So configured, a pharmaceutical fluid such as a water, saline, a solution, a diluent, a final drug product, etc., may enter the inlet 124 of the housing 104 through the sterile closure cap and connector assembly 108, pass through the filter membrane 170, and beyond the outlets 126, 129 of the housing 104 and retention channel 123, respectively, and finally through the bridging channel 127 and into the product chamber 110. This filled state of the chamber 110 is depicted schematically in FIG. 2A, for example. As mentioned above, the filter membrane 170 of the filtration device 103 is configured to sterilize the pharmaceutical fluid passing into the product bag 100. Specific examples of the filter membrane 170 will be described in more detail below.

It should be appreciated that in the embodiment depicted in FIGS. 1 and 2A-2C, the inlet 124 of the filtration device 103 is located at the bottom side 109b, which is opposite the hanging opening 117, of the product bag 100. This orientation, relative to gravity, can be beneficial when filling the product bag 100 with solutions that tend to foam such as certain antibiotics because this bottom fill procedure can reduce aeration during filling.

Once the desired amount of pharmaceutical fluid is introduced into the chamber 110 of the product bag 100 in the manner described, some embodiments of the disclosure may benefit from sealing the product chamber 110 off from the retention chamber 123 and optionally cutting the filtration device 103 away from the bag 109 and performing an integrity test of the filtration membrane 170. In one embodiment, the next step in the process is to seal the chamber 110 and, more particularly, to seal the first and second film layers 105a, 105b together across the bridging channel 127 to create a bridge seal 135, which is illustrated in FIG. 2B. The bridge seal 135 effectively closes and hermetically seals the chamber 110, protecting the sterility of the fluid disposed therein.

Next, if the process includes testing the filter membrane 170, a portion of the retention section 121 of the perimeter seal 107, which includes the embedded filtration device 103, can be cut off of the product bag 100, as shown in FIG. 2C.

It is important that the cut occurs along a line L (shown in FIG. 2B) that is parallel to the longitudinal axis A of the retention section 121 and through a center portion of the bridge seal 135. The resultant product bag 100 can be seen in FIG. 2C, where a remaining portion 137 of the perimeter seal 107 remains along the left side 111a of the bladder 102.

As also shown in FIG. 2C, prior to performing an integrity test on the filter membrane 170, an end portion 139 of the retention section 121 can be cut away to provide direct exposure to the outlet 126 of the filtration device 103. To ensure that the filter membrane 170 performed properly, and that the fluid in the chamber 110 is sufficiently sterile, a filter integrity test can be performed on the filter membrane 170. For example, after the filtration device 103 and retention section 121 are separated from the product bag 100, a filter testing device (not shown) may be pre-programmed or controlled to perform a filter integrity test on the filter membrane 170. Examples of filter integrity tests might include a bubble point test, a pressure degradation test, a water intrusion test, a water flow test, or any suitable test known in the art. A pressure degradation test is a method for testing the quality of a filter either before or after the filter has been used. In the preferred embodiment, the filter membrane 170 is tested after the solution passes through the filter membrane 170 and into the bladder 102 of the product bag 100. To perform the filter integrity test using a pressure degradation test procedure, a test head (not shown) engages the inlet 124 of the housing 104 and applies an air pressure of a predetermined value to filter membrane 170. In one embodiment, the pre-determined value is the pressure where gas cannot permeate the filter membrane 170. A pressure sensor, or other method of measuring the integrity of the filter, is located within the test head and measures the pressure decay or diffusion rate through the filter membrane 170. The results from the integrity test are assessed to determine the quality of the filter membrane 170, and therefore the quality of the solution that previously passed through the filter membrane 170 and into the product bag 100. If the pressure sensor measures a decay or a unexpected rate of decay, then the filter membrane 170 fails the test and it can be determined that the solution in the product bag is unsatisfactory. Alternatively in a bubble point test, the test head gradually increases the pressure applied to the filter membrane 170, and the increase in pressure is measured in parallel with the diffusion rate of the gas through the filter membrane 170. Any disproportionate increase in diffusion rate in relation to the applied pressure may indicate a hole or other structural flaw in the filter membrane 170, and the filtration device 103 would fail the integrity test.

Thus, it can be appreciated that the disclosed arrangement of the retention section 121, filtration device 103, and bridge seal 135 advantageously facilitates the filter integrity test, which allows for a determination to be made with a high degree of certainty that the fluid in the product bag is either sterile or has the potential of being compromised.

The product bag 100 described with respect to FIGS. 1 and 2A-2C is described as including a product chamber 110. In some embodiments, the product chamber 110 can be completely empty and sterile prior to introducing any pharmaceutical fluid into the chamber 110 through the filtration device 130. In other embodiments, the product chamber 110 can be pre-filled with a sterile product concentrate such as a medicament or nutrient concentrate in the form of a powder, a granulate, a gel, a foam, a liquid, etc. In such embodiments, introducing the pharmaceutical fluid into the chamber 110 can include introducing a diluent into the chamber 110 to reconstitute the concentrate into a form that can then be administered to a patient. While the product bag 100 in FIGS. 1 and 2A-2C is described as including a bladder 102 with a single product chamber 110, other embodiments can include multiple chamber portions.

Figure 2:
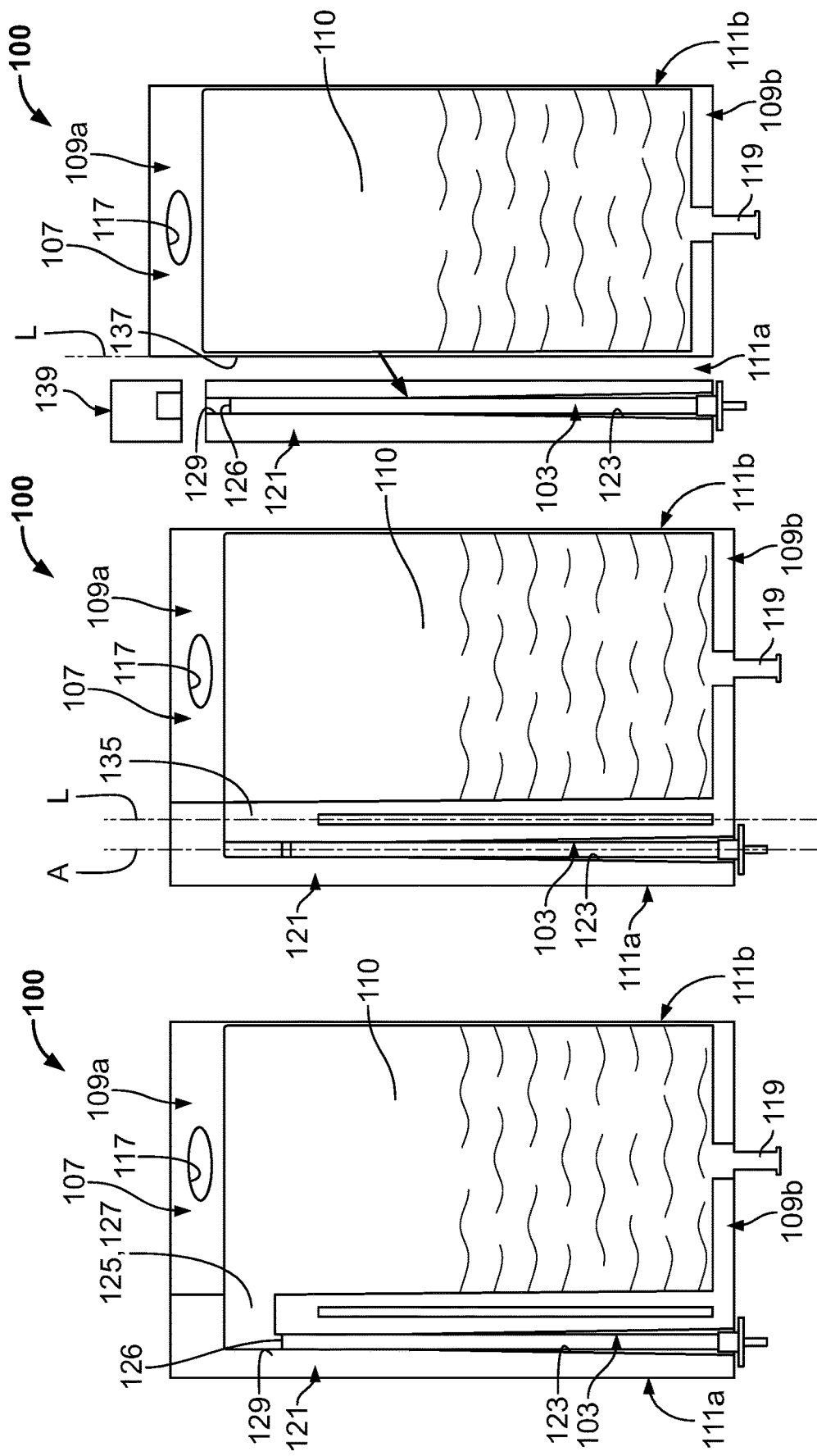
FIGS. 2A-2C are front view of the filtered product bag of FIG. 1 showing the various steps of a fill, seal and cut process.
Figure 3:
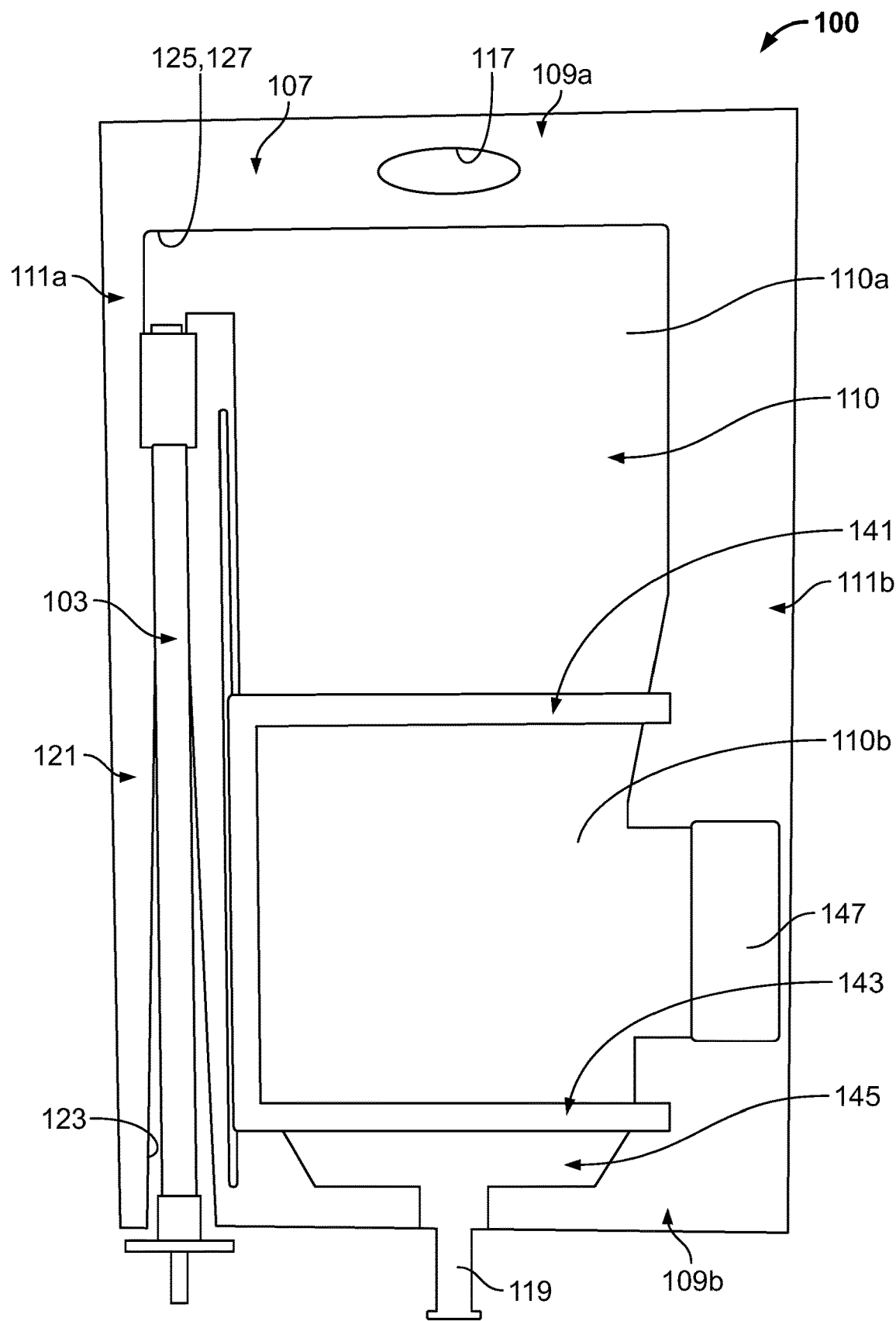
FIG. 3 is a front view of a second embodiment of a filtered product bag constructed in accordance with the principles of the present disclosure.

For example, FIG. 3 depicts an alternative product bag 100 constructed in accordance with the principles of the present disclosure and being substantially similar to the product bag 100 described with reference to FIGS. 1 and 2A-2C. Thus, for the sake of simplicity, similar components will be identified by similar reference numerals and primarily only the distinctions will be described in any detail. Like the product bag 100 of FIG. 1, the product bag 100 in FIG. 3 includes a bladder 102 with a perimeter seal 107 defining a product chamber 110. But unlike FIG. 1, the product chamber 110 of the product bag 100 of FIG. 3 includes first and second chamber portions 110a, 110b, isolated from each other by at least one intermediate seal 141 extending between the left and right sides 111a, 111b of the perimeter seal 107. The intermediate seal 141 is preferably a peel seal that maintains its integrity until a certain hydraulic pressure in the chamber 110 forces the seal to break. That is, the first chamber portion 110a is disposed at an upper portion of the chamber 110 in proximity to the top side 109a of the product bag 100, and the second chamber portion 110b is disposed at lower portion of the chamber 110 in proximity to the bottom side 109b of the product bag 100. So arranged, the first chamber portion 110a is in fluid communication with the retention channel 123 and filtration device 103 by way of the bridge channel 127. In the disclosed embodiment, the second chamber portion 110b is also adapted to be in fluid communication with the outlet port 119 of the product bag 100.

With the product bag 100 arranged as depicted in FIG. 3, the second chamber portion 110b can be entirely empty or pre-filled with a product concentrate to be reconstituted prior to patient administration. In the pre-filled embodiment, this product concentrate can be filled through a side port 147 in an aseptic filling environment. The side port 147 extends through the perimeter seal 107 in the right side 111b of the product bag 100, and is heat sealed or otherwise permanently bonded closed after filling such that the product concentrate introduced into the second chamber portion remains sterile.

In some embodiments, a buffer seal 143 can also be provided to seal the second chamber portion 110b off from the outlet port 119 until administration is desired. The buffer seal 143 extends across the chamber 110 between portions of the perimeter seal 107 at the left and right sides 111a, 111b. Like the intermediate seal 141 discussed above, the buffer seal 143 is preferably a peel seal that maintains its integrity until a certain hydraulic pressure in the chamber 110 forces the seal to break. As can be seen, in some embodiments, the inclusion of a buffer seal 143 results in the chamber 110 of the product bag 100 further including a buffer chamber portion 145 disposed below the second chamber portion 110b opposite the buffer seal 143.

Introducing pharmaceutical fluid into the first chamber portion 110a by way of the filtration device 103 of the product bag 100 of FIG. 3 occurs in the same manner as introducing fluid into the chamber 100 of the product bag 100 of FIGS. 1 and 2A-2C. Thus this process need not be repeated. After fluid resides in the first chamber portion 110a, the bridging channel 127 is sealed to form the bridge seal 135 (not shown in FIG. 3) and the filter membrane 170 of the filtration device 103 is optionally cut off of the product bag 100 and tested for integrity. If the filter membrane 170 passes the integrity test, a user can than reconstitute the product concentrate pre-filled in the second chamber portion 110*b*. This is achieved by manually manipulating the first chamber portion 1110*a*, which is filled with fluid, to create hydraulic pressures that act on the intermediate seal 141 and ultimately break the intermediate seal 141. When the intermediate seal 141 breaks, the pharmaceutical fluid mixes with the concentrate in the second chamber portion 110*b* to reconstitute the product. Once the product is sufficiently mixed and reconstituted, additional manual manipulation of the chamber 110 can be performed to create hydraulic pressures that act on and break the buffer seal 143 allowing the product to ultimately flow into and through the buffer chamber 145 and to the outlet port 119 for patient administration. As can be appreciated, the product bag 100 depicted in FIG. 3 is also a bottom fill bag where the inlet 124 of the filtration device 103 is located at the bottom side 109*b* of the product bag 100 near the outlet port 119. As mentioned above with respect to FIGS. 1 and 2A-2C, this bottom fill configuration can be beneficial in reducing aeration when introducing pharmaceutical fluids that may have a tendency to foam into the product chamber 110.

Advantages of the configuration depicted in FIGS. 1-3 include elimination of tubing segments on the container and filter assembly, increased pack factor for gamma sterilization of the empty containers, ability to use longer filters for same pack factor to reduce fill time, and elimination of container fill tube vestige.

Figure 4:
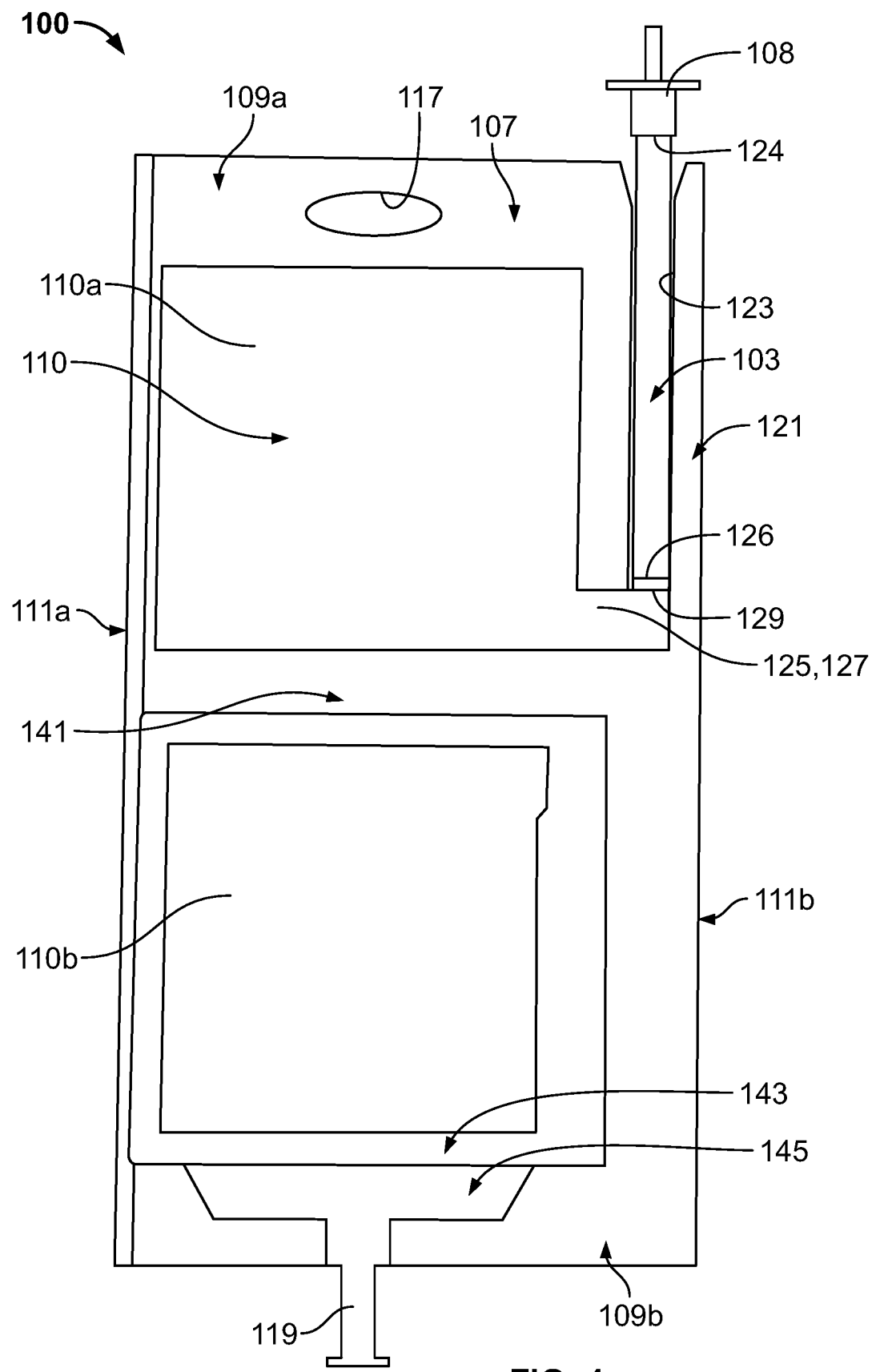
FIG. 4 is a front view of a third embodiment of a filtered product bag constructed in accordance with the principles of the present disclosure.
Figure 4A:
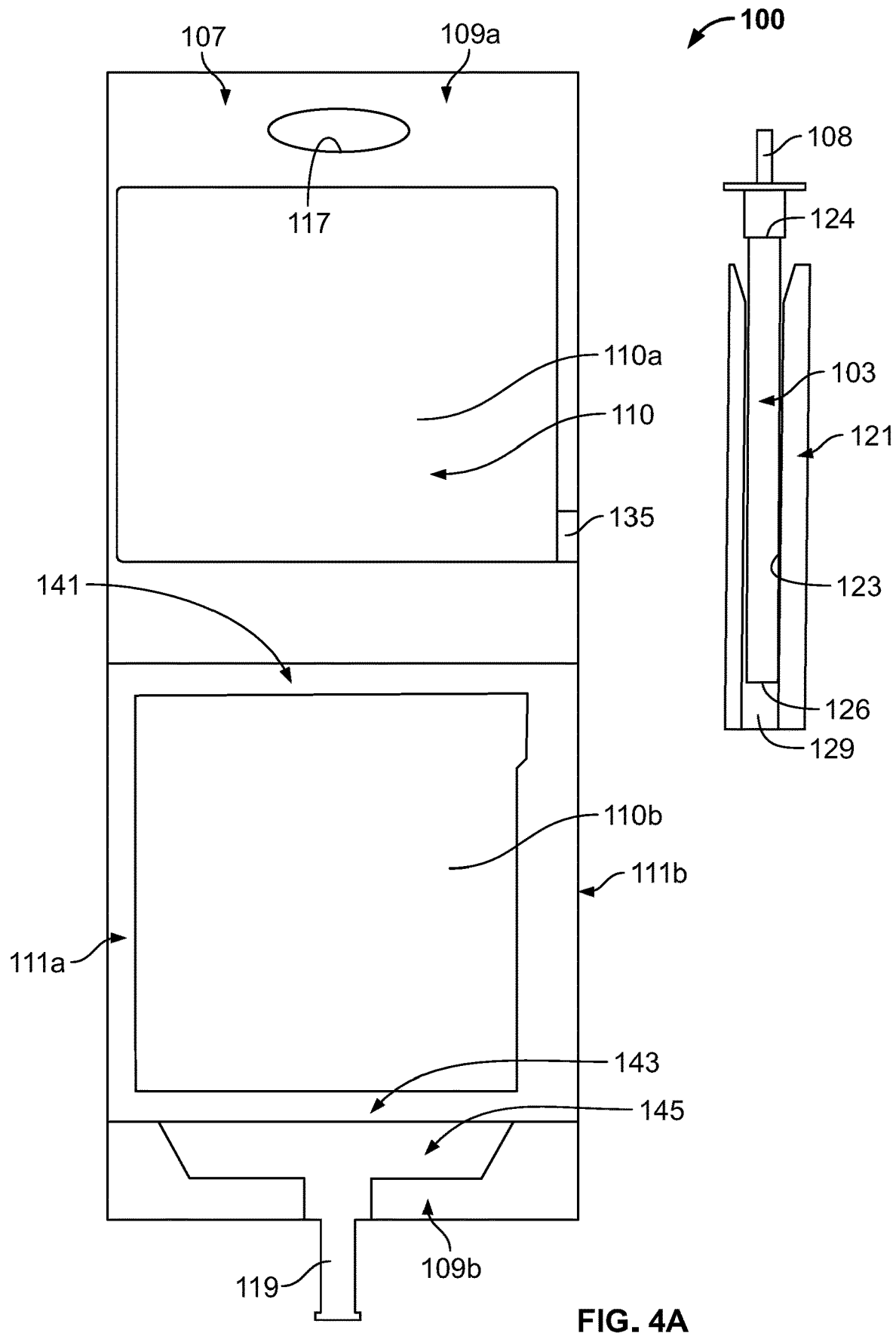
FIG. 4A is a front view of the filtered product bag of FIG. 4 after having been filled, sealed, and cut.

While FIGS. 1-3 all depict bottom fill product bags 100, other embodiments can include different configurations. For example, FIGS. 4 and 4A depict one alternative product bag 100 including a bladder 102 with a perimeter seal 107 and a chamber 110 with multiple chamber portions 110*a*, 110*b*, 145, same as the product bag 100 of FIG. 3. As such, those aspects will not be repeated. Unlike FIG. 3, however, the product bag of FIG. 4 includes the filtration device 103 being arranged in a manner that its inlet 124 is disposed on the top side 109*a* of the bag 100 in proximity to the hanger opening 117 and opposite the outlet port 119. Moreover, as depicted in FIG. 4, the retention section 121 of the perimeter seal 107, which retains the filtration device 103, is disposed on the right side 111*b* of the bag 100. But this is merely a product of the orientation of the bag in FIG. 4. Further, the filtration device 103 in FIG. 4 is depicted as having a shorter longitudinal dimension than in FIGS. 1-3 because the outlet 126 of the filtration device 103 must align with the outlet 129 of the retention channel 123 and bridging channel 127 to communicate with the first chamber portion 110*a*. All other aspects of the relationship between the filtration device 103, retention section 121, and retention channel 123 remain the same as that described above with respect to the same components in FIGS. 1-3. For example, filling of the first chamber portion 110*a* is achieved by introducing fluid through the filtration device 103. Then the bridging channel 127 can be sealed to form a bridge seal 135. For testing the integrity of the filtration device 103, the retention section 121 of the perimeter seal 107 containing the filtration device 103 can be cut off of the product bag along line L located between the retention channel 123 and the chamber 110 such that the chamber 110 remains sealed, as shown in FIG. 4A. Finally, before the filtration device 103 can be integrity tested, a portion of the retention section 121 located beyond the outlet 126 of the filtration device 130 must be cut off, as depicted in FIG. 4A, to expose the outlet 126 and facilitate the testing procedure as described above. While the top-fill bag 100 of FIG. 4 is depicted as having a chamber 110 with multiple chamber portions, alternative embodiments of the bag can have a single chamber such as in FIG. 1. The remainder of the reconstitution and administration process for the product bag 100 in FIGS. 4 and 4A is identical to that described above with respect to FIG. 3. Although not expressly depicted, the scope of the disclosure also includes single chamber top-fill product bags 100 with the filtration device 103 embedded as described herein.

As mentioned, the filter membrane 170 of the filtration device 103 of the present disclosure is configured to sterilize fluid as is passes through the filtration device 103 and into the product bag 100. So configured, the sterile fluid in the product bag 100 can be subsequently administered directly to a patient. The filtration device 103 and the filter membrane 170 can take many different forms and the scope of the present disclosure is not necessarily limited to any one or more.

Figure 5:
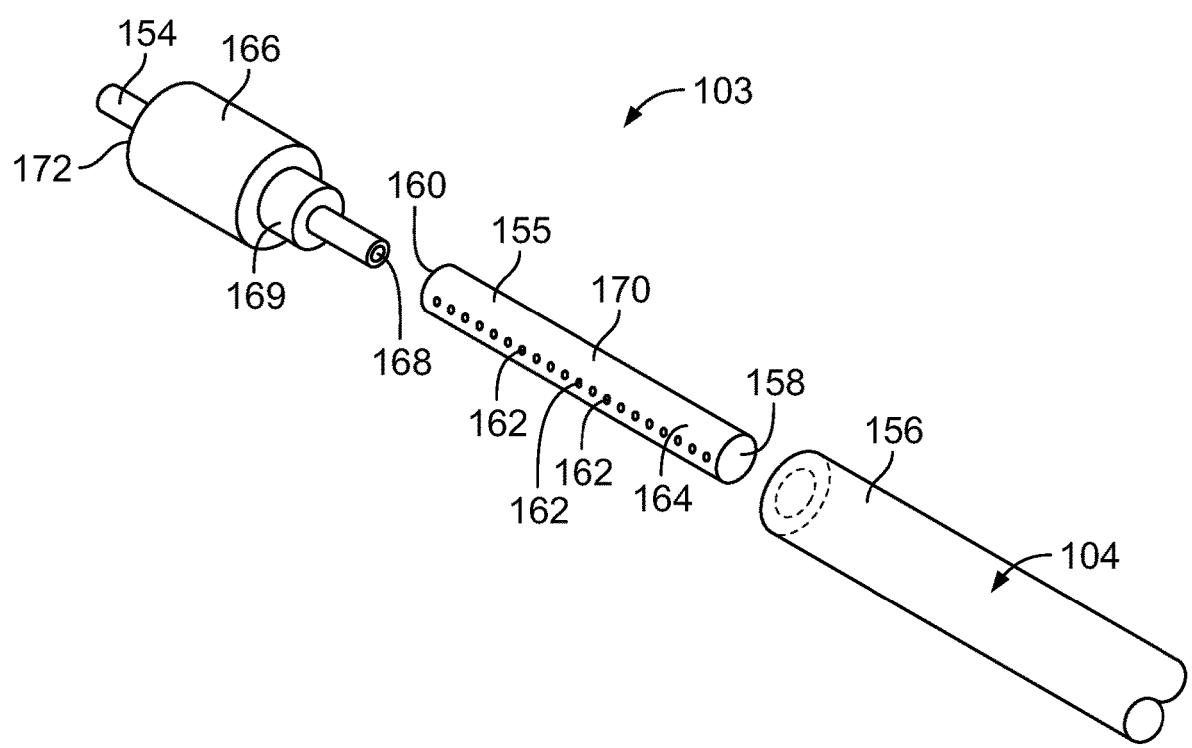
FIG. 5 is an expanded isometric view of the filter and stem depicted in FIGS. 3 and 4.
Figure 6:
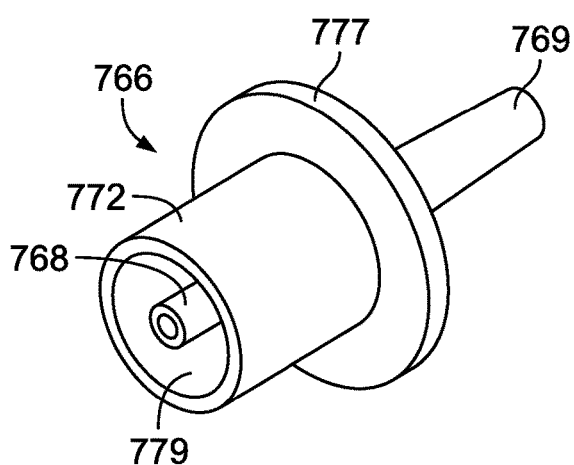
FIG. 6 is a perspective view of an alternative connector for use with a filter and stem such as that disclosed in FIGS. 3-5.
Figure 7:
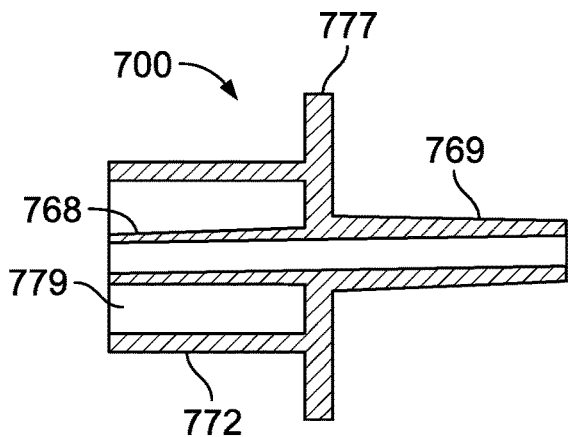
FIG. 7 is a side cross-sectional view of the connector of FIG. 6.
Figure 8:
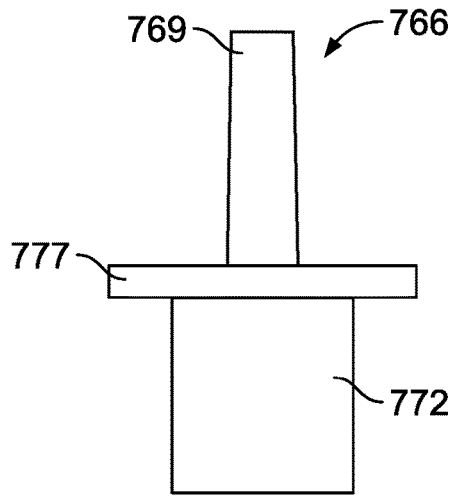
FIG. 8 is a side view of the connector of FIG. 6.
Figure 9:
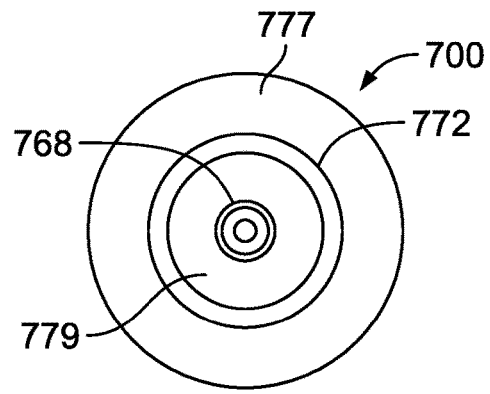
FIG. 9 is a bottom view of the connector of FIG. 8.
Figure 10:
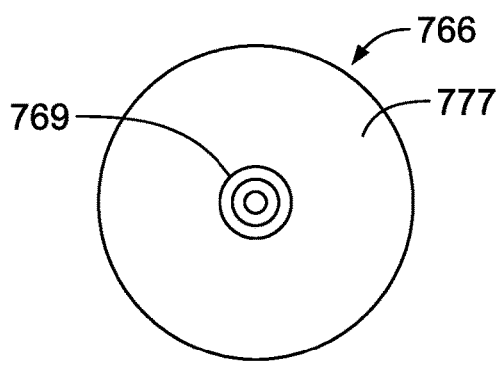
FIG. 10 is a top view of the connector of FIG. 8.

For example, FIG. 5 depicts one embodiment of the filtration device 103 where the housing 104 comprises a stem 156, and a hollow connector 166 is used to secure the stem 156 and the filter membrane 170 together. The connector 166 can be part of, or coupled to, the sterile closure cap and connector assembly 108 described above in FIGS. 1-4. The filter membrane 170 includes an open inlet end 160 sealingly connected to an open outlet end 168 of the hollow connector 166. The connection may be achieved by gluing the open inlet end 160 of the filter membrane 170 to the open outlet end 168 of the connector 166 with, for example, an epoxy resin, a polyurethane resin, a cyanoacrylate resin, a UV curing acrylic adhesive, or a solvent for the material of the hollow connector 166 such as cyclohexanone. In the version depicted, the open outlet end 168 of the connector 166 comprises a hollow cylindrical member that fits inside of and is fixed to the open inlet end 160 of the filter membrane 170. As such, an outer diameter of the open outlet end 168 of the connector 166 is substantially similar to or slightly smaller than an inner diameter of the open inlet end 160 of the filter membrane 170. In some versions, the open inlet end 160 of the filter membrane 170 may be welded to the open outlet end 168 of the connector 166 by, for example, heat welding (e.g., introducing a hot conical metal tip into the open inlet end 150 of the filter membrane 170 to partially melt it), laser welding if the hollow connector 166 is made from a material that absorbs laser radiation, mirror welding, ultrasound welding, and friction welding. Alternately, the filter membrane 170 may be inserted into a mold, and a thermoplastic polymer may be injection-molded around it to form the hollow connector 166. Other designs and configurations for connecting the filter membrane 170 to the connector 166 are intended to be within the scope of the present disclosure.

The hollow connector 166 further includes a fluid inlet 169. A pharmaceutical fluid can be fed via a connected fluid supply line, for example, into the fluid inlet 169 of the hollow connector 166. In some versions, the fluid inlet 169 can include a Luer type fitting or other standard medical fitting. The pharmaceutical fluid can then travel through the hollow connector 166 and exit into the filter membrane 170 through the open outlet end 168 of the hollow connector 166. The hollow connector 166 also includes a sealing surface 172 to which the stem 156 is attached. The sealing surface 172 in this version is cylindrical and has a diameter larger than a diameter of the open outlet end 168, and is disposed generally concentric with the open outlet end 168. In fact, in this version, the outer diameter of the sealing surface 172 is generally identical to or slightly smaller than an inner diameter of the stem 156. So configured, the stem 156 receives the sealing surface 172 and extends therefrom to surround and protect the filter membrane 170 without contacting the surface 164 of the filter membrane 170. The stem 156 can be fixed to the sealing surface 172 with adhesive (e.g., a UV curing acrylic adhesive), epoxy, welding, bonding, etc. The stem 156 receives the pharmaceutical solution after it passes through the pores 162 in the filter membrane 170. From there, the now filtered solution passes into the bladder 152.

FIGS. 6-10 illustrate an alternative hollow connector 766, similar to connector 166, for securing the stem 156 and the hollow fiber filter membrane 170 of FIGS. 3-5 together. The connector 766 includes an open outlet end 768 carried by a stem structure that extends in a first direction from a bearing plate 777 and is adapted to be sealingly connected to the open inlet end 160 of the filter membrane 170. The connection may be achieved by gluing the open inlet end 160 of the filter membrane 170 to the open outlet end 768 of the connector 766 with, for example, an epoxy resin, a polyurethane resin, a cyanoacrylate resin, a UV curing acrylic adhesive, or a solvent for the material of the hollow connector 766 such as cyclohexanone. In the version depicted, the stem structure of the open outlet end 768 of the connector 766 comprises a hollow cylindrical member that fits inside of and is fixed to the open inlet end 160 of the filter membrane 170. As such, an outer diameter of the open outlet end 768 of the connector 766 is substantially similar to or slightly smaller than an inner diameter of the open inlet end 160 of the filter membrane 170. In some versions, the open inlet end 160 of the filter membrane 170 may be welded to the open outlet end 768 of the connector 766 by, for example, heat welding (e.g., introducing a hot conical metal tip into the open inlet end 150 of the filter membrane 170 to partially melt it), laser welding if the hollow connector 766 is made from a material that absorbs laser radiation, mirror welding, ultrasound welding, and friction welding. Alternately, the filter membrane 170 may be inserted into a mold, and a thermoplastic polymer may be injection-molded around it to form the hollow connector 766. Other designs and configurations for connecting the filter membrane 170 to the connector 766 are intended to be within the scope of the present disclosure.

The hollow connector 766 further includes a fluid inlet 769, which is also a stem structure, extending in a second direction (opposite the first direction) from the bearing plate 777. A pharmaceutical fluid can be fed via a connected fluid supply line, for example, into the fluid inlet 769 of the hollow connector 766. In some versions, the fluid inlet 769 can include a Luer type fitting or other standard medical fitting. The pharmaceutical fluid can then travel through the hollow connector 766 and exit into the filter membrane 170 through the open outlet end 768 of the hollow connector 766.

The hollow connector 766 also includes a sealing surface 772 to which the stem 156 is attached. The sealing surface 772 in this version is a cylindrical shroud extending from the bearing plate 777 in the first direction and has a diameter larger than a diameter of the open outlet end 768. The sealing surface 772 is disposed generally concentric with the open outlet end 768. As such, in this embodiment, the shroud of the sealing surface 772 surrounds the stem structure of the open outlet end 768 such that an annular gap 779 resides between the two. In fact, in this version, the outer diameter of the sealing surface 772 is generally identical to or slightly smaller than an inner diameter of the stem 156. So configured, the sealing surface 772 of the connector 766 can be received by the stem 156 such that the stem 156 extends therefrom to surround and protect the filter membrane 170 without contacting the surface 164 of the filter membrane 170. The stem 156 can be fixed to the sealing surface 772 with adhesive (e.g., a UV curing acrylic adhesive), epoxy, welding, bonding, etc. The stem 156 receives the pharmaceutical fluid after it passes through the pores 162 in the filter membrane 170. From there, the now filtered fluid passes into the product bag 100 of any of FIGS. 1-4.

While the foregoing version of the filter membrane 170 has been described as including a single filter membrane 170, in other embodiments within the scope of the present disclosure, the filter membrane 170 may include multiple filter membranes 170. A few non-limiting examples of multiple membrane filters will be discussed below. Finally, in some embodiments, the connector 166 in FIG. 5 can include a sterile closure cap 154 covering the solution inlet 168 to prevent contaminants from entering the product bag prior to being filled.

In one version of the foregoing assembly of FIG. 5, and as mentioned, the stem 156 includes an inner diameter that is larger than an outer diameter of the filter membrane 170, and the stem 156 includes a longitudinal dimension that is larger than a longitudinal dimension of the filter membrane 170. As such, when the stem 156 and filter membrane 170 are assembled onto the connector 166, the filter membrane 170 resides entirely within (i.e., entirely inside of) the stem 156 and a gap exists between the inner sidewall of the stem 156 and the outer sidewall of the filter membrane 170. As such, fluid passing into the filter membrane 170 passes out of the plurality of pores 162 and flows without obstruction through the gap and along the inside of the stem 156 to the bladder. In some versions, the stem 156 can be a flexible tube, a rigid tube, or can include a tube with portions that are flexible and other portions that are rigid. Specifically, in some versions, a stem 156 with at least a rigid portion adjacent to the filter membrane 170 can serve to further protect the filter membrane 170 and/or prevent the filter membrane 170 from becoming pinched or kinked in a flexible tube. In other versions, such protection may not be needed or desirable. In one embodiment, the stem 156 has an internal diameter in the range of approximately 2.5 mm to approximately 8 mm, and a longitudinal dimension in the range of approximately 5 cm to approximately 30 cm. In one embodiment, the internal diameter of the stem 156 is about 0.2 to about 3 mm larger than the outer diameter of the filter membrane 170. And, the filter membrane 170 has an outer diameter in the range of approximately 2.3 mm to approximately 5 mm, a longitudinal dimension in the range of approximately 3 cm to approximately 420 cm, and a wall thickness in the range of approximately 150 μm to approximately 500 μm. Furthermore, in one version each of the plurality of pores 162 in the filter membrane 170 have a diameter less than or equal to approximately 0.2 microns. In some versions, each pore has a diameter less than or equal to a value in a range of approximately 0.1 microns to approximately 0.5 microns, for instance, approximately 0.2 to approximately 0.4 microns. In some versions, each pore has a diameter that is less than or equal to approximately 0.22 microns. In some versions, each pore has a diameter that is less than or equal to a value in a range of approximately 0.1 microns to approximately 0.2 microns. In some versions, each pore has a diameter that is less than or equal to a value in a range of approximately 0.1 microns to approximately 0.22 microns. These pore sizes coupled with the disclosed geometrical dimension of the stem 156 and filter membrane 170 ensure acceptable flow rates through the filter membrane 170 for filling the product bags with patient injectable solutions such as sterile water, sterile saline, etc. In other versions, any or all of the dimensions could vary depending on the specific application.

Suitable materials for the filter membrane 170 can include polyolefins (e.g., PE, PP), polyvinylidene fluoride, polymethylmethacrylate, polyacrylonitrile, polysulfone, and polyethersulfone. In some embodiments within the scope of the present disclosure, the filter membrane 170 may be comprised of a blend of polysulfone or polyethersulfone and polyvinylpyrrolidone. In other embodiments within the scope of the present disclosure, the filter membrane 170 can include a polymer containing cationic charges, e.g. polymers bearing functional groups like quaternary ammonium groups. A suitable example for such polymers is polyethyleneimine. The filter membrane 170 may be manufactured by known techniques including, e.g., extrusion, phase inversion, spinning, chemical vapor deposition, 3D printing, etc. Suitable materials for the stem 156 include PVC, polyesters like PET, poly(meth)acrylates like PMMA, polycarbonates (PC), polyolefins like PE, PP, or cycloolefin copolymers (COC), polystyrene (PS), silicone polymers, etc.

Additional details regarding some possible versions of the filter and the specific construction of the membrane, for example, can be found in European Patent Application No. EP16152332.9, entitled FILTER MEMBRANE AND DEVICE, filed Jan. 22, 2016, and additionally in PCT/EP2017/051044, entitled FILTER MEMBRANE AND DEVICE, filed Jan. 19, 2017, the entire contents of each of which are expressly incorporated herein by reference.

Thus far, the hollow fiber membrane 170 in FIG. 5, for example, has been described as being located within the stem 156. In other embodiments, the filter membrane 170 may include its own housing or other support structure, which is coupled to the stem 156 either in place of the connector 166 in FIG. 5 or connector 766 in FIGS. 6-10, or at a location between two portions of the stem 156.

Figure 11:
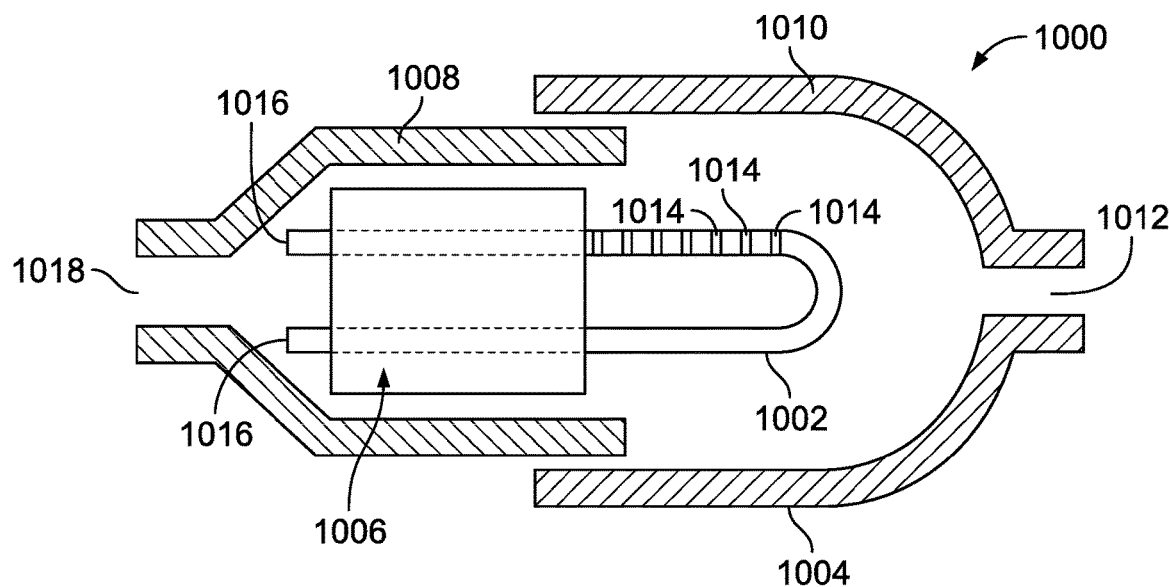
FIG. 11 is a front view of a filter for a sterile product bag having a single looped hollow fiber membrane contained within a filter body.

For example, FIG. 11 is a front view of a filter assembly 1000 for a product bag (not pictured) having a single U-shaped hollow fiber filter membrane 1002 contained within a filter body 1004. The filter membrane 1002 is secured to a filter membrane housing 1006 in the U-shaped configuration with an adhesive (i.e., a UV curing acrylic adhesive), an epoxy, welding, bonding, or other means. The filter membrane housing 1006 is connected to the filter body 1004 at an outlet portion 1008 of the filter body 1004. An inlet portion 1010 is sealably connected to the outlet portion 1008 of the filter body 1004 at a joint or other seam. The inlet portion 1010 of the filter body 1004 has an inlet 1012 by which a pharmaceutical fluid may enter the filter assembly 1000. The pharmaceutical fluid then enters the filter membrane 1002 through a plurality of pores 1014, travels through the filter membrane 1002, exits the filter membrane 1002 at filter membrane outlets 1016, and exits the filter body 1004 at filter outlet 1018. The filter outlet 418 may then be connected to the bladder (not pictured) via the stem 256 of a product bag (not pictured). In FIG. 11, the flow of fluid through the assembly 1000 has been described as moving from the inlet 1012 of the inlet portion 1010 to the outlet 1018 of the outlet portion 1008. However, the same assembly 400 could be used in the opposite direction such that fluid enters the outlet 1018 of the outlet portion 1008 and exits the inlet 1012 of the inlet portion 1010. In this alternative configuration, fluid would first enter the inlet 1018, pass into the filter membrane 1002 at the filter membrane outlets 1016, and exit through the pores 1014 and finally the inlet 1012.

Figure 12:
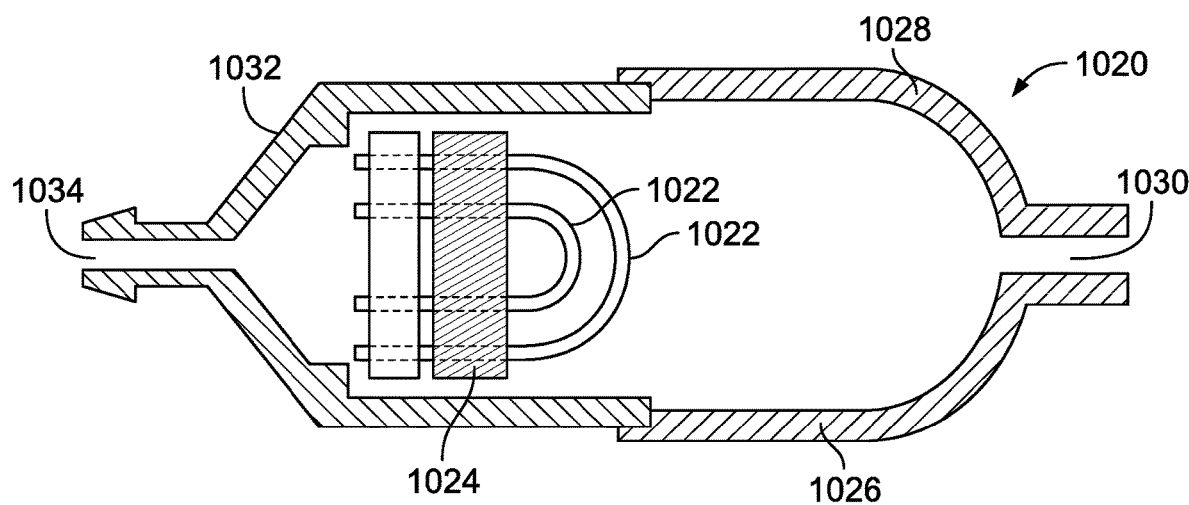
FIG. 12 is a front view of a filter for a sterile product bag having a plurality of looped hollow fiber membranes contained within a filter body.

FIG. 12 is an alternate embodiment of the filter assembly 1000 depicted in FIG. 11. In FIG. 12, the filter 1020 includes two U-shaped hollow fiber filter membranes 1022 are secured to a filter membrane housing 1024 in the U-shaped configuration with an adhesive (i.e., a UV curing acrylic adhesive), an epoxy, welding, bonding, or some other means. The filter membranes 1022 and filter membrane housing 1024 are contained within a filter body 1026 having an inlet portion 1028 with inlet 1030 sealably connected to an outlet portion 1032 having filter outlet 1034. In other embodiments, a filter may include more than two U-shaped hollow fiber filter membranes arranged as depicted in FIGS. 11 and 12. In FIG. 12, like in FIG. 11, the flow of fluid through the assembly 1000 has been described as moving from the inlet portion 1028 to the outlet portion 1032. However, the same assembly 1000 could be used in the opposite direction such that fluid enters the outlet portion 1032 and exits the inlet portion 1028 as described above relative to FIG. 11.

FIG. 13 is a further alternative filter assembly. Specifically, in FIG. 13, a plurality of linear membrane filters 502 are secured directly together in a parallel side-by-side configuration for what can be referred to as a fiber bundle. The filters 502 in FIG. 13 can be secured together with adhesive (i.e., a UV curing acrylic adhesive), epoxy, welding, bonding, etc. In other versions, the plurality of filters 502 can be manufactured together as one piece by way of any of the manufacturing techniques described above.

FIG. 14 provides another alternative in which a securement device 504 includes a number of blocks defining a plurality of grooves 506 identical to the number of hollow fiber membrane filters 502. The blocks of the securement device 504 may be sandwiched together and used to hold the plurality of hollow fiber membrane filters 502 in the side-by-side configuration. The securement device 504 depicted in FIG. 14 allows for two sets of the hollow fiber membrane filters 502 of FIG. 13 to be stacked relative to each other. The fiber bundle including the membrane filters 502 and the securement device 504 may be placed in a filter body, such as that discussed with respect to FIGS. 11 and 12.

FIG. 15 is an isometric view of another version of a fiber bundle 600 for a product bag (not pictured) having a plurality of parallel hollow fiber membrane filters 502 similar to FIGS. 13 and 14, but wherein the parallel filters 502 are arranged in a circular pattern by a circular holder 504. The fiber bundle 600 may be placed in a filter body, such as that discussed with respect to FIGS. 11 and 12.

FIGS. 16-17 and FIGS. 18-20 illustrate two additional devices for coupling fiber bundles to a stem in accordance with the present disclosure. FIGS. 16-17 discloses a connector 866 for connecting a three-fiber bundle to a stem. Specifically, the connector 866 includes a first hollow body 866$a$ and a second hollow body 866$b$. The first body 866$a$ includes a solution inlet 869, which is a stem structure, extending from a bearing plate 877. A pharmaceutical fluid can be fed via a connected fluid supply line, for example, into the fluid inlet 869 of the first hollow body 866$a$ of the connector 866. In some versions, the fluid inlet 869 can include a Luer type fitting or other standard medical fitting.

The hollow connector 866 also includes a sealing surface 872 to which the stem 156 is attached. The sealing surface 872 in this version is a cylindrical shroud extending from the bearing plate 877 in a direction opposite to a direction of extension of the fluid inlet 869. The sealing surface 872 is disposed generally concentric with the fluid inlet 869. As such, in this embodiment, the shroud of the sealing surface 872 defines a cylindrical cavity (not shown in the drawings) for receiving a portion of the second hollow body 866$b$ of the connector 866.

The second hollow body 866b, as depicted, includes a support plate 880 and three open outlet ends 868 extending from the support plate 880. Additionally, the support plate 880 includes an outer diameter that is essentially the same as or slightly smaller than an inner diameter of the cavity of the shroud of the sealing surface 872 such that when assembled, the support plate 880 is positioned into the cavity. In one version, the support plate 880 includes a seal member 882 around its periphery to form a fluid tight seal with the inner surface of the shroud of the sealing surface 872 when inserted into the cavity. Friction, adhesive, or some other means may retain the support plate 880 in connection with the shroud of the sealing surface 872.

As mentioned, the second body 866b includes three open outlet ends 868 extending from the support plate 880. Each open outlet end 868 is adapted to be sealingly connected to an open inlet end 160 of one of three filters 155. The connection may be achieved by gluing open inlet ends 160 of the filters 155 to the open outlet ends 868 with, for example, an epoxy resin, a polyurethane resin, a cyanoacrylate resin, a UV curing acrylic adhesive, or a solvent for the material of the hollow connector 766 such as cyclohexanone. In the version depicted, the stem structure of the open outlet ends 868 of the connector 866 comprises a hollow cylindrical member that fits inside of and is fixed to the open inlet ends 160 of the filters 155. As such, an outer diameter of the open outlet ends 868 is substantially similar to or slightly smaller than an inner diameter of the open inlet ends 160 of the filters 155. In some versions, the filters 155 may be welded to the open outlet ends 868 of the connector 866 by, for example, heat welding (e.g., introducing a hot conical metal tip into the open inlet ends 150 of the filters 155 to partially melt it), laser welding if the hollow connector 866 is made from a material that absorbs laser radiation, mirror welding, ultrasound welding, and friction welding. Alternately, the filters 155 may be inserted into a mold, and a thermoplastic polymer may be injection-molded around it to form the hollow connector 866. Other designs and configurations for connecting the filters 155 to the open outlet ends 868 are intended to be within the scope of the present disclosure.

Finally, as with previously described embodiments, the sealing surface 872 of the connector 866 can be received by the stem 156 such that the stem 156 extends therefrom to surround and protect the filters 155 without contacting the surfaces 164 of the filters 155. The stem 156 can be fixed to the sealing surface 872 with adhesive (e.g., a UV curing acrylic adhesive), epoxy, welding, bonding, etc. The stem 156 receives the pharmaceutical solution after it passes through the pores 162 in the filter membrane 170. From there, the now filtered solution passes into the bladder 152 in the same manner described above with respect to FIGS. 3-5.

Figure 18:
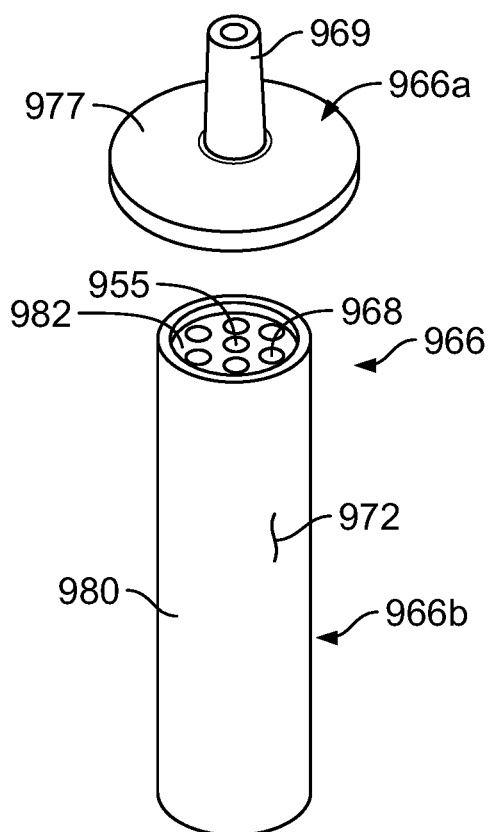
FIG. 18 is a exploded perspective view of another alternative connector for use with a seven-filter filter bundle.
Figure 19:
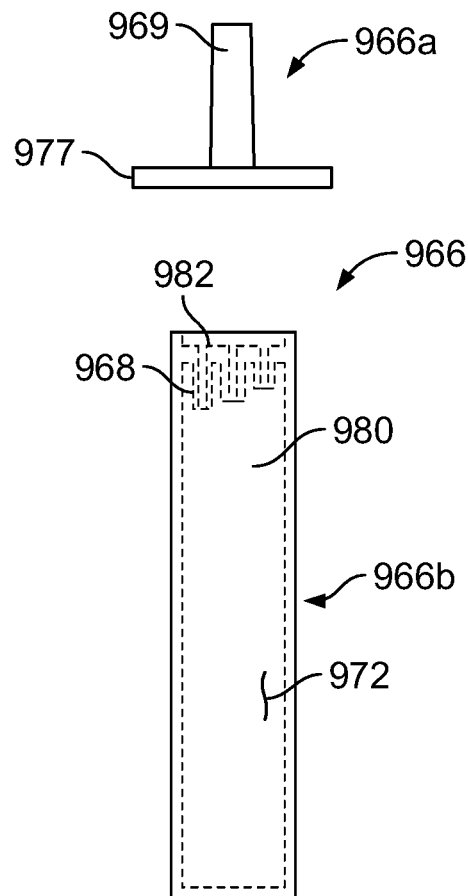
FIG. 19 is a side exploded view of the connector of FIG. 18.
Figure 20:
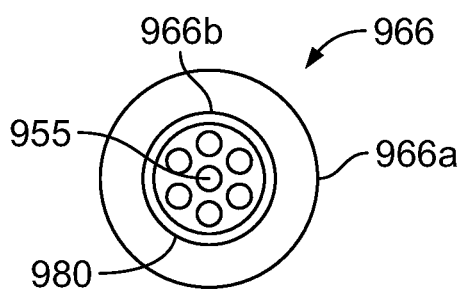
FIG. 20 is a bottom view of the connector of FIG. 19.

FIGS. 18-20 discloses a connector 966 for connecting a seven-fiber bundle to a stem. Specifically, the connector 966 includes a first hollow body 966a and a second hollow body 966b that can be connected to the first hollow body 966a with an adhesive or via other means. The first body 966a includes a solution inlet 969, which is a stem structure, extending from a bearing plate 977. A pharmaceutical fluid can be fed via a connected fluid supply line, for example, into the fluid inlet 969 of the first hollow body 966a of the connector 966. In some versions, the fluid inlet 969 can include a Luer type fitting or other standard medical fitting.

The second hollow body 966b, as depicted, includes a hollow cylindrical support collar 980 in which seven hollow fiber membrane filters 955 can be disposed parallel to each other, as shown in FIGS. 18 and 20. In one version, the support collar 980 can include a support plate 982 carrying seven open outlet ends 968 extending into the collar 980 for connecting to the filters 955 in a manner similar to that described above regarding FIGS. 16-17. The connection may be achieved by gluing the filters 955 to the open outlet ends 968 with, for example, an epoxy resin, a polyurethane resin, a cyanoacrylate resin, a UV curing acrylic adhesive, or a solvent for the material of the hollow connector 966 such as cyclohexanone. In the version depicted, the stem structure of the open outlet ends 868 of the connector 866 comprises a hollow cylindrical member that fits inside of and is fixed to the filters 955. As such, a diameter of the open outlet ends 968 is substantially similar to or slightly smaller than an inner diameter of the filters 955. In some versions, the filters 955 may be welded to the open outlet ends 968 of the connector 966 by, for example, heat welding (e.g., introducing a hot conical metal tip into the filters 955 to partially melt it), laser welding if the hollow connector 966 is made from a material that absorbs laser radiation, mirror welding, ultrasound welding, and friction welding. Alternately, the filters 955 may be inserted into a mold, and a thermoplastic polymer may be injection-molded around it to form the hollow connector 966. Other designs and configurations for connecting the filters 955 to the open outlet ends 968 are intended to be within the scope of the present disclosure.

Finally, the collar 980 of this embodiment includes a sealing surface 972 that can be received by the stem 156 such that the stem 156 extends therefrom. The stem 156 can be fixed to the sealing surface 972 with adhesive (e.g., a UV curing acrylic adhesive), epoxy, welding, bonding, etc. The stem 156 receives the pharmaceutical fluid after it passes through the pores 162 in the filters 955. From there, the now filtered fluid passes into the bladder 152 in the same manner described above with respect to FIGS. 3-5.

From the foregoing, it can be seen that various filtering arrangements can serve the principles of the present disclosure including introducing fluid to the product bag in a sterilized manner. While certain representative versions of the claimed subject matter have been described herein for purposes of illustrating the invention, it will be apparent to those skilled in the art that various changes in the devices and methods disclosed may be made without departing from the spirit and scope of the invention, which is defined by the following claims and is not limited in any manner by the foregoing description.

The invention claimed is:

1. A method of sterilizing and introducing fluid into a product bag, the method comprising:

providing a bladder comprising opposing first and second film layers defining a sterile product chamber, the first and second film layers sealed together along a perimeter seal extending along at least a portion of a perimeter of the bladder, the perimeter seal including at least one break defining a bridging channel in fluid communication with the sterile product chamber;

providing a filtration device having an inlet end adapted for receiving a fluid to be sterilized, and an outlet end in fluid communication with the sterile product chamber via the bridging channel, the filtration device having a filter membrane with a nominal pore size in a range of approximately 0.1 µm to approximately 0.5 µm;

introducing a pharmaceutical fluid into the sterile product chamber through the filtration device and bridging channel such that a sterile pharmaceutical fluid resides within the sterile product chamber; and sealing the opposing first and second film layers together across the bridging channel to create a bridge seal to maintain the sterilized pharmaceutical fluid in the sterile product chamber.

2. The method of claim 1, further comprising cutting the filtration device off of the product bag.

3. The method of claim 2, wherein the step of cutting the filtration device off of the product bag comprises cutting across the bridging seal.

4. The method of claim 2, further comprising performing a filter integrity test on the filter membrane after the step of cutting the filtration device off of the product bag.

5. The method of claim 4, wherein the step of performing the filter integrity test comprises performing one of a pressure degradation test, a bubble point test, a water intrusion test, or a water flow test.

6. The method of claim 1, wherein the step of introducing the pharmaceutical fluid into the sterile product chamber through the filtration device comprises introducing the pharmaceutical fluid through a plurality of filter membranes.

* * * * *